United States Patent [19]

McLean

[11] Patent Number: 5,686,668
[45] Date of Patent: Nov. 11, 1997

[54] SYSTEM AND METHOD OF ULTRASONIC INSPECTION OF TUBULAR MEMBERS

[76] Inventor: Ted McLean, 3503 Cedar Knolls Dr., Suite A, Kingwood, Tex. 77399

[21] Appl. No.: 727,262

[22] Filed: Oct. 8, 1996

[51] Int. Cl.⁶ .................................................. G01N 29/26
[52] U.S. Cl. ............................. 73/622; 73/637; 73/638; 73/639
[58] Field of Search ........................ 73/622, 636, 637, 73/638, 639, 640, 641, 635, 597, 598, 599, 600, 618

[56] References Cited

U.S. PATENT DOCUMENTS

| 4,041,773 | 8/1977 | Hauldren et al. | 73/622 |
|---|---|---|---|
| 4,108,004 | 8/1978 | Murakami | 73/638 |
| 4,213,345 | 7/1980 | Dufour | 73/637 |
| 4,312,230 | 1/1982 | Bricker et al. | 73/638 |
| 4,893,512 | 1/1990 | Tanimoto et al. | 73/622 |
| 4,995,320 | 2/1991 | Sato et al. | 73/638 |
| 5,549,004 | 8/1996 | Nugent | 73/622 |

FOREIGN PATENT DOCUMENTS

| 2105466 | 3/1983 | United Kingdom | 73/622 |

*Primary Examiner*—Hezron E. Williams
*Assistant Examiner*—Nashmiya Ashraf
*Attorney, Agent, or Firm*—Harrison & Egbert

[57] ABSTRACT

A cart for inspecting a drill pipe having a platform with an ultrasonic inspection unit thereon, a first pair of wheels connected to the platform so as to move the platform longitudinally along the drill pipe relative to a rotation of the drill pipe, and a bearing connected to the platform at a location distal of the first pair of wheels. The bearing serves to support the platform above an adjacent drill pipe and allows the platform to move longitudinally along the adjacent drill pipe in correspondence with the movement of the first pair of wheels. The first pair of wheels are canted at an angle relative to the longitudinal axis of the drill pipe. A sensor wheel extends outwardly of the platform and rotates during the movement of the platform along the drill pipe. The platform has at least one handle extending upwardly from the platform. The bearing includes a pair of rollers that have an axis of rotation which is transverse to the longitudinal axis of the adjacent drill pipe.

19 Claims, 5 Drawing Sheets

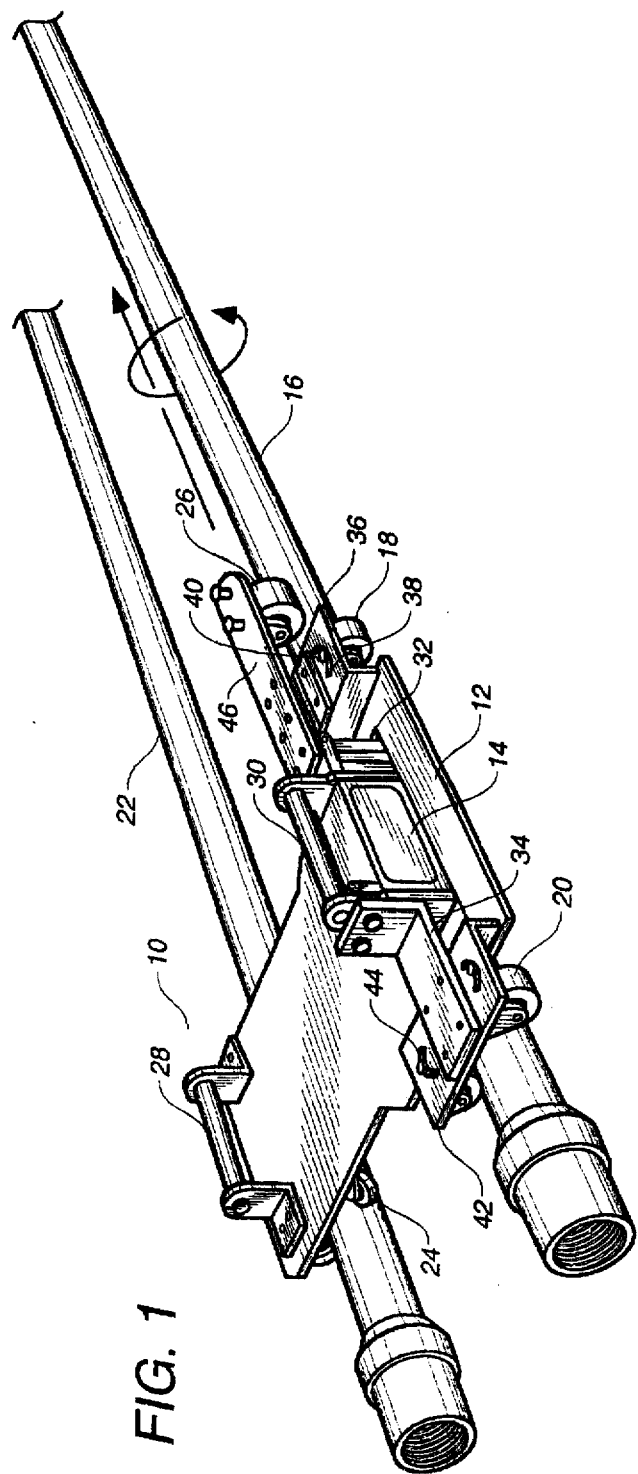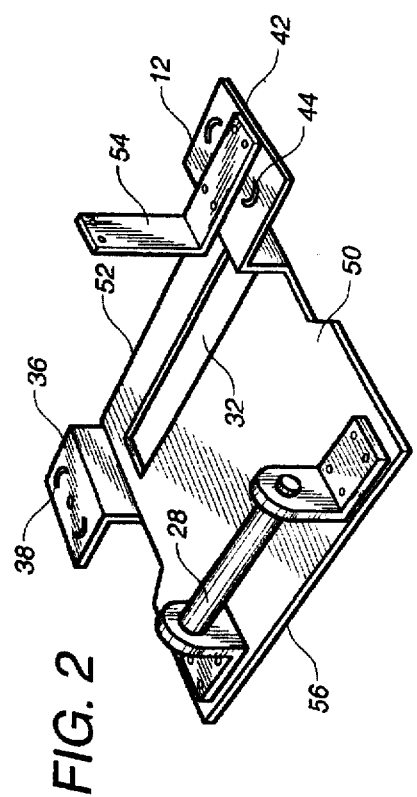
FIG. 1
FIG. 2

SYSTEM AND METHOD OF ULTRASONIC INSPECTION OF TUBULAR MEMBERS

TECHNICAL FIELD

The present invention relates to the ultrasonic inspection of tubular members. More particularly, the present invention relates to apparatus and methods for non-destructively inspecting an entire length of a tubular member. Furthermore, the present invention relates to systems whereby the existing tubular member supports an ultrasonic inspection unit.

BACKGROUND ART

Drill pipe is used for the drilling of oil and gas wells. Typically, a large number of drill pipes extend from the surface of the earth down to the drilling bit. When each of the drill pipes is connected in end-to-end relationship, the "drill string" is formed.

During the drilling of oil wells, it is very important that each of the drill pipes has proper integrity and strength. As a result, an ultrasonic inspection of each of the drill pipes is necessary and important. Conventionally, ultrasonic inspection is carried out so as to determine whether or not any minute cracks or deformations exist in the drill pipe. If cracks and/or deformations are found in the drill pipe, then the drill pipe should not be used. Ultrasonic inspection involves transmitting an ultrasonic wave through the drill pipe and receiving the reflected signal of the ultrasonic beam. Various diagnostic programs and devices are used so as to properly analyze the results of the ultrasonic inspection.

At present, hand-held ultrasonic units are used manually by an operator to inspect the ends of the drill pipe. This area is known as the critical end area because this area is where most of the failures occur. Since the distance to be inspected at the end of the drill pipe is short, the ultrasonic beam is narrow. The ultrasonic inspection unit travels slowly and is held by the operator. There are various ultrasonic inspection units that carry out complete inspection of drill pipe. However, these units are large trailer mounted units or fixed units which are not easily transportable. These inspection units are mostly installed in pipe mills or large pipe yards. Typically, the pipe is delivered to the inspection unit. These units function by running the pipe on conveyors through one end of the inspection unit, under the inspection sensors, and out the other side.

It is an object of the present invention to provide a method and apparatus for the inspection of tubular members.

It is another object of the present invention to provide a method and apparatus for the inspection of tubular members which serves to inspect the entire length of the tubular member.

It is a further object of the present invention to provide a method and apparatus for the inspection of tubular members which allows for on-site inspection of the tubular member.

It is a further object of the present invention to provide a method and apparatus for the inspection of tubular members which allows the tubular member being inspected to act as a bridge on which an inspection cart runs the entire length of the tubular member.

It is a further object of the present invention to provide a method and apparatus for the inspection of tubular members which is easy to use, relatively inexpensive, and labor efficient.

These and other objects and advantages of the present invention will become apparent from a reading of the attached specification and appended claims.

SUMMARY OF THE INVENTION

The present invention is a cart for the inspecting of tubular members that comprises a platform having a means thereon for receiving a non-destructive inspection unit, a first wheel connected to the platform for moving the platform longitudinally along the tubular member relative to a rotation of the tubular member, and a bearing means connected to the platform at a location distal the first wheel means. The bearing means serves to support the platform above an adjacent tubular member and for allowing the platform to move longitudinally along the adjacent tubular member in correspondence with the moving of the first wheel means.

The first wheel means includes a first pair of wheels positioned at one end of the platform. The first pair of wheels has an axis of rotation which is canted at an angle relative to a longitudinal axis of the tubular member. A second pair of wheels is positioned at an end of the platform opposite the first pair of wheels. The second pair of wheels is canted at the same angle as the first pair of wheels relative to the longitudinal axis of the tubular member. The first pair of wheels is rotatably supported below a bar. The bar is adjustably pivotally connected to the platform so as to change the angle of cant to a desired angle. The platform has a first arcuate slot and a second arcuate slot formed therein. The bar has a first guide member extending upwardly through the first arcuate slot and a second guide member extending upwardly through the second arcuate slot. Each of the guide members has a means for fixing a position of the guide member in the slot.

The cart of the present invention also includes a sensor wheel means which extends outwardly of the platform. The sensor wheel means rotates during the movement of the platform along the tubular member. The sensor wheel means serves to transmit an ultrasonic signal through the tubular member. In particular, the sensor wheel means includes a sensor wheel which is rotatably mounted onto an arm extending outwardly of the platform. The sensor wheel has a surface extending downwardly from the arm so as to contact the tubular member. The sensor wheel has an axis of rotation which is canted at the same angle as the first pair of wheels.

The platform has at least one handle member affixed thereto and extending upwardly from the platform. The platform also includes an area for receiving a non-destructive inspection unit. This area is formed between the first pair of wheels and the second pair of wheels so as to be generally adjacent to a surface of the tubular member. The bearing means is connected to an opposite side of the cart from the first wheel means. In particular, the bearing means includes a first roller which is rotatably connected to the platform and extends downwardly therefrom. This first roller has a surface for contacting a surface of the adjacent tubular member. The first roller has an axis of rotation transverse to a longitudinal axis of the adjacent tubular member. A second roller is rotatably connected to the platform and extends downwardly therefrom. The second roller has a surface for contacting a surface of the adjacent tubular member. The second roller is radially offset from the first roller relative to the tubular member. The second roller also has an axis of rotation which is transverse to the longitudinal axis of the adjacent tubular member.

The present invention is also a method of ultrasonically inspecting a tubular member which comprises the steps of: (1) placing a first tubular member onto a drive roller of a tubular member support rack; (2) positioning a second tubular member in generally parallel relationship to the first tubular member on the tubular member support rack; (3) placing an inspection cart onto the first and second tubular members such that the inspection cart has a pair of canted wheels contacting a surface of the first tubular member and a bearing contacting a surface of the second tubular member; (4) rotating the first tubular member such that the inspection cart moves longitudinally along the first tubular member and the second tubular member, and (5) transmitting inspection data from the inspection unit as the inspection cart moves along the first tubular member.

The method of the present invention further includes the step of lifting the inspection cart from the first and second tubular members after the inspection cart reaches a desired destination along the first tubular member. The first tubular member is then removed from the drive roller and the second tubular member is then moved into the drive roller. A third tubular member is positioned into generally parallel relationship to the second tubular member on the tubular member support rack. The inspection cart is placed onto the second and third tubular members such that the pair of canted wheels contacts a surface of the second tubular member and the bearing contacts a surface of the third tubular member. The second tubular member is rotated such that the inspection cart moves horizontally along the second tubular member and the third tubular member. Ultrasonic inspection data is transmitted from the inspection unit as the inspection cart moves along the second tubular member.

BRIEF DESCRIPTION OF THE DRAWINGS

FIG. 1 is a perspective view of the inspection cart of the present invention as applied onto a pair of tubular members.

FIG. 2 is a perspective view of the platform of the cart of the present invention.

DETAILED DESCRIPTION OF THE INVENTION

Figure 3:
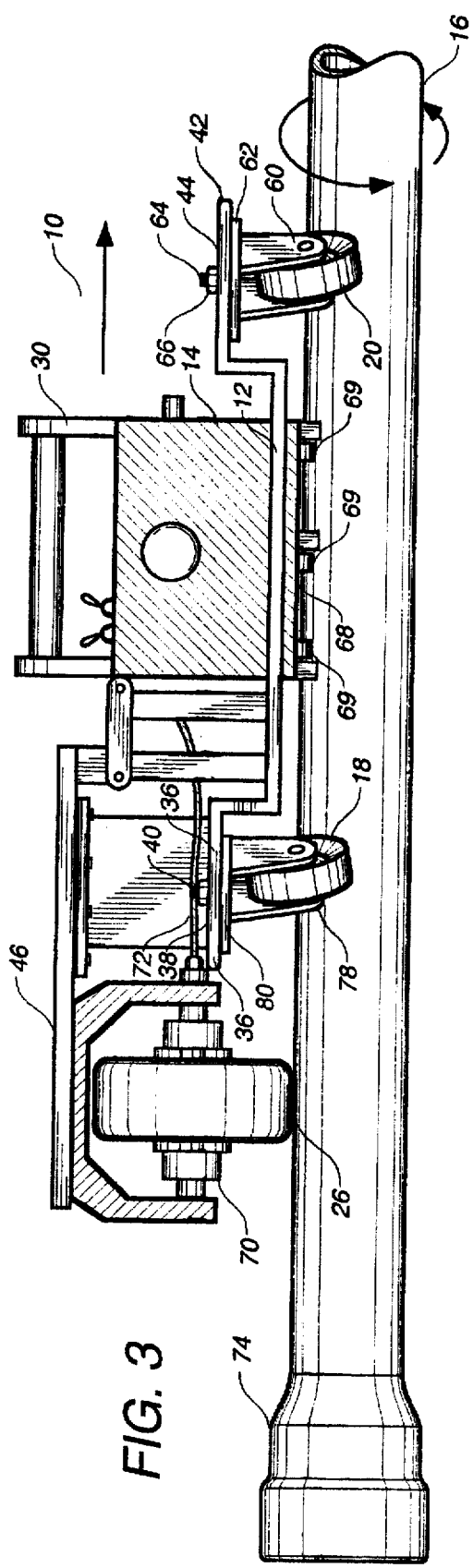
FIG. 3 is a side elevational view of the inspection cart as placed upon a tubular member.

Referring to FIG. 1, there is shown at 10 the system of the present invention for the inspection of tubular members, in particular, drill pipe. The system 10 of the present invention includes a platform 12 having a non-destructive inspection unit 14 placed thereon. The cart 12 is supported upon a first tubular member 16 through the use of a first pair of wheels 18 and a second pair of wheels 20. The opposite side of the platform 12 is supported on the second tubular member 22 by a bearing arrangement 24. A sensor wheel 26 extends outwardly from the platform 12 so that the wheel 26 contacts a surface of the first tubular member 16. In the present application, certain terms are employed for purposes of simplicity. As used herein, the term "platform" can refer to flat surfaces, connector members or other structures that connect the wheels 18 and 20 and also support the inspection unit 14. Also, as used herein, the term "tubular member" can include drill pipe, casings, tubes, and solid bar stock having a circular cross-section. Furthermore, the term "bearing arrangement" can include ball bearings, small wheels, or other rotatable items that can ride on a surface of the tubular member.

In FIG. 1, it can be seen that the platform 12 is a generally flat platform 11 that has a handle 28 extending upwardly from a top surface of the platform 12 generally adjacent to the second tubular member 22 and above the bearings 24. A second handle 30 is affixed above the inspection unit 12 the side of the platform 12 in alignment with the first pair of wheels 18 and the second pair of wheels 20. The platform 12 includes a receiving area 32 formed therein so as to be positioned between the first pair of wheels 18 and the second pair of wheels 20. The receiving area 32 serves to receive the inspection unit 14 therein and to allow the inspection unit to be directly supported on a surface of the tubular member 16. The platform 12 is configured so as to move in close proximity to a top surface of the tubular members 16 and 22.

The inspection unit 14 is a non-destructive inspection unit. Various types of non-destructive inspection units can be employed in the present invention. For example, the platform 12 could receive ultrasonic inspection devices, electromagnetic inspection devices, hall effect inspection units and, possibly, magnetic resonance imaging units. However, the preferred embodiment of the present invention contemplates ultrasonic inspection units. These ultrasonic inspection units serve to transmit an ultrasonic wave through a liquid medium and through the wall of the tubular member 16 so that the reflection of the ultrasonic wave will be indicative of flaws or deformations in the material of the tubular member 16. Normally, the inspection unit 14 is used as a hand held unit for the inspection of the ends of the drill pipe, as described herein previously in the "Background Art". Suitable bracketing 34 is provided so as to secure the ultrasonic inspection unit 14 within the receiving area 32 of the platform 12. The inspection unit has small wheels which support the inspection unit on the tubular member. The ultrasonic signal is transmitted by the sensor wheel 26.

The first pair of wheels 18 are positioned at one end of the platform 12. The first pair of wheels 18 has an axis of rotation which is canted at an angle relative to the longitudinal axis of the tubular member 16. A more detailed illustration of such canting is provided in FIG. 4. Similarly, the second pair of wheels 20 is positioned at an end of the platform 12 opposite the first pair of wheels 18. The second pair of wheels 20 is also canted at the same angle as the first pair of wheels 18 with respect to the longitudinal axis of the tubular member 16. Importantly, it can be seen that the first pair of wheels 18 is supported by a L-shaped member 36 which extends outwardly of the platform 12. The L-shaped member 36 includes an arcuate slot 38 formed therein. The wheels 18 include a guide member 40 which extends into the arcuate slot 38. The guide member 40 is suitable for fixing in a position along the arcuate slot 38 so as to fix a cant of the first pair of wheels 18 relative to the longitudinal axis of the tubular member 16. A similar L-shaped bracket 42 is provided so as to support the second pair of wheels 20 in a position relative to the tubular member 16. The L-shaped bracket 42 also includes arcuate slots 44 which receive a guide member from the second pair of wheels 20. The guide member in the arcuate slot is suitable for fixing the cant of the second pair of wheels 20 at a same angle as the cant of the first pair of wheels 18.

In FIG. 1, it can be seen that the sensor wheels 26 extend outwardly from the platform 12 by an arm 46. Arm 46 is positioned in a location adjacent to the inspection unit 14 and the handle 30. The area 46 is flexible so as to be able to ride up the end of upset pipe. The sensor wheel 26 serves to rotate during the movement of the platform 12 along the tubular member 16. The sensor wheel 26 is connected to the inspection unit 14 by suitable electronics so as to transmit an ultrasonic signal into the tubular member 14. The sensor wheel 26 can be canted at the same angle as the wheels 18. A suitable slot can be provided in the area 46 to accommodate the angular adjustment of the sensor wheel 26.

FIG. 2 is an isolated view of the platform 12. Initially, it can be seen that the platform 12 includes a flat surface 50. The flat surface 50 will extend between the first tubular member 16 and the second tubular member 22. The rectangular receiving area 32 is illustrated as in a location adjacent to side 52 of the platform 12. A first L-shaped bracket 36 extends upwardly and outwardly from one end of the flat surface 50. The L-shaped bracket 36 includes arcuate slots 38 for the receiving of the guide members from the first pair of wheels. A second L-shaped bracket 42 extends outwardly from an opposite end of the flat surface 50. The second L-shaped bracket 42 also includes arcuate slots 44 for receiving the guide members of the second pair of wheels 20. An L-shaped member 54 is affixed to the top surface of the second L-shaped bracket 42. The L-shaped member 54 is suitable for the attachment of handle 30 and for the receiving of the inspection unit 14 within the receiving area 32. The handle 28 is affixed to the flat surface 50 and extends upwardly therefrom. The handle 28 is positioned adjacent to the side 56 of the surface 50.

FIG. 3 shows the configuration of the cart 10 as positioned on the first tubular member 16. Initially, it can be seen that the second pair of wheels 20 are rotatably supported within a caster 60. The caster 60 is affixed to a bar 62. A guide member 64 extends upwardly from the bar 62 and outwardly of the L-shaped bracket 42 through the arcuate slot 44. As can be seen, the guide member 64 is a threaded member which includes a nut 66 for securing the guide member 64 in a proper position within the arcuate slot 44. By the loosening of the nut 66, the angle of cant of the second pair of wheels 20 can be suitably adjusted. By changing the angle of cant, the rate of movement of the cart 10 relative to the tubular member 16 can be varied.

The L-shaped bracket 42 extends outwardly from the platform 12. The inspection unit 14 is supported on the top surface of the platform 12. It can be seen that the inspection unit 14 includes a bottom surface 68 which is positioned in very close proximity to the exterior surface of the tubular member 16. Small wheels 69 on the bottom of the inspection unit 14 allow the inspection unit to be supported on the tubular member 16. The handle 30 extends upwardly from the top surface of the inspection unit 14.

An arm 46 extends outwardly from the inspection unit 14 and from the platform 12. Arm 46 serves to support the sensor wheel 26 in a location forward of the first pair of wheels 18. The sensor wheel 26 is rotatably mounted within frame 70 so as to allow the wheel 26 to rotate as the cart 14 traverses the length of the tubular member 16. An electrical line 72 extends from the axis of rotation of the wheel 26 so as to provide sensing information to the inspection unit 14. The sensor wheel 26 operates in a similar fashion as sensor wheels of conventional hand-held inspection units. A suitable means of data transfer can be connected to the inspection unit 14 so as to allow the ultrasonic inspection data to be transmitted to an instrument package exterior of the tubular member rack. Additionally, a liquid hose can be connected to the sensor wheel 26 so that the liquid medium can be applied to the surface of the tubular member.

It can be seen in FIG. 3 that the first pair of wheels 18 are canted at an angle relative to the longitudinal axis of the tubular member 16. The first pair of wheels 18 are received within casters 78 so as to allow the wheels 18 to rotate freely therein. The casters 78 are mounted on a bar 80. The guide member 40 extends upwardly through the arcuate slot 38 on the L-shaped bracket 36. The guide member 40 is fixed in a position within the arcuate slot 38 by the use of a nut.

Figure 4:
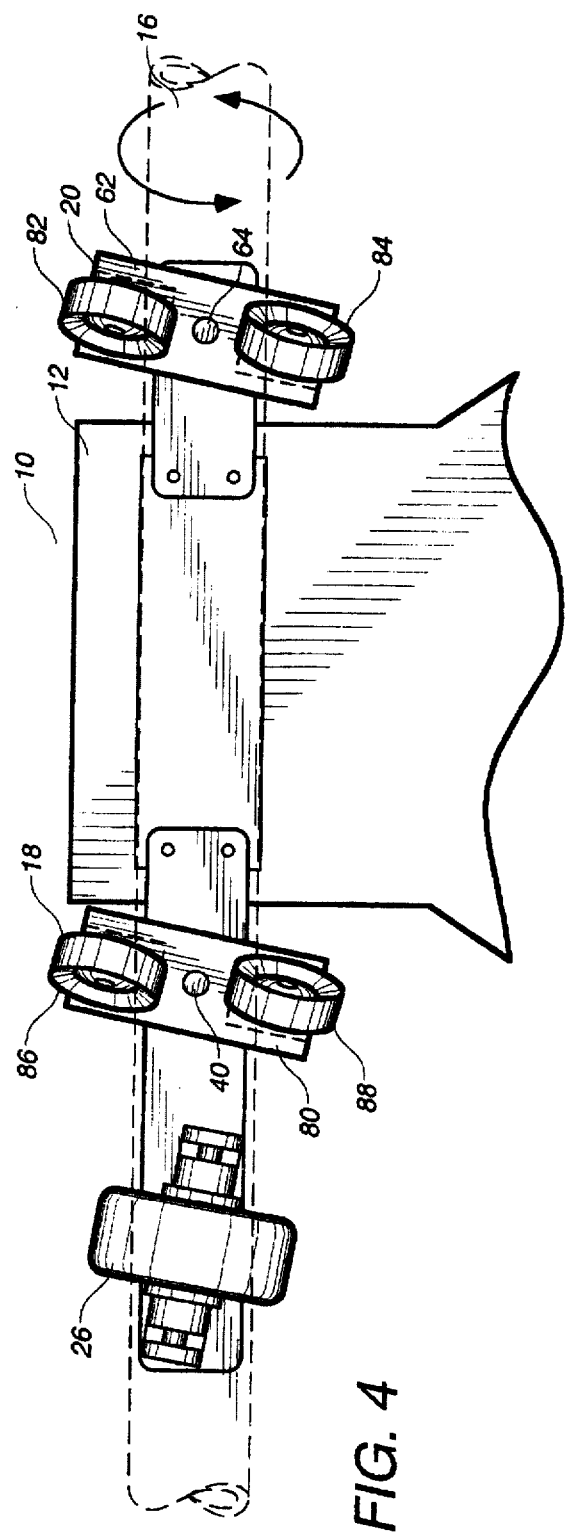
FIG. 4 is a bottom view of the inspection cart of the present invention with the tubular member shown in transparent fashion.

In FIG. 4, the tubular member 16 is illustrated in transparent fashion so that the actual canting of the first pair of wheels 18 and the second pair of wheels 20 can be properly seen. Initially, it can be seen that the second pair of wheels 20 includes a first wheel 82 and a second wheel 84 which are mounted on bar 62. The guide member 64 is mounted in the center of the bar 62 so as to allow a desired amount of pivotal movement so that the wheels 82 and 84 can be properly canted. Similarly, the first pair of wheels 18 includes a first wheel 86 and a second wheel 88. Wheels 86 and 88 are supported on bar 80. The guide member 40 is formed centrally of the bar 80 so as to allow a proper pivoting of the first pair of wheels 18. Ideally, the first pair of wheels 18 and the second pair of wheels 20 should have a similar cant so that the wheels will cause the platform 12 of the cart 10 to move along the length of the tubular member 16 when the tubular member 16 is rotated. If the wheels 18 and 20 were not canted, then the platform 12 of the cart 10 would remain in a stationary position on the tubular member 16.

It can be seen in FIG. 4 that the sensor wheel 26 is also canted at an angle similar to the angle of the first pair of wheels 18 and the second pair of wheels 20. As such, the sensor wheel 26 will not resist the movement of the cart 10 during the traversing of the tubular member 16. The sensor wheel 26, wheels 86 and 88 of the first pair of wheels 18, and wheels 82 and 84 of the second pair of wheels 20 will all contact a surface of the tubular member 16.

Figure 5:
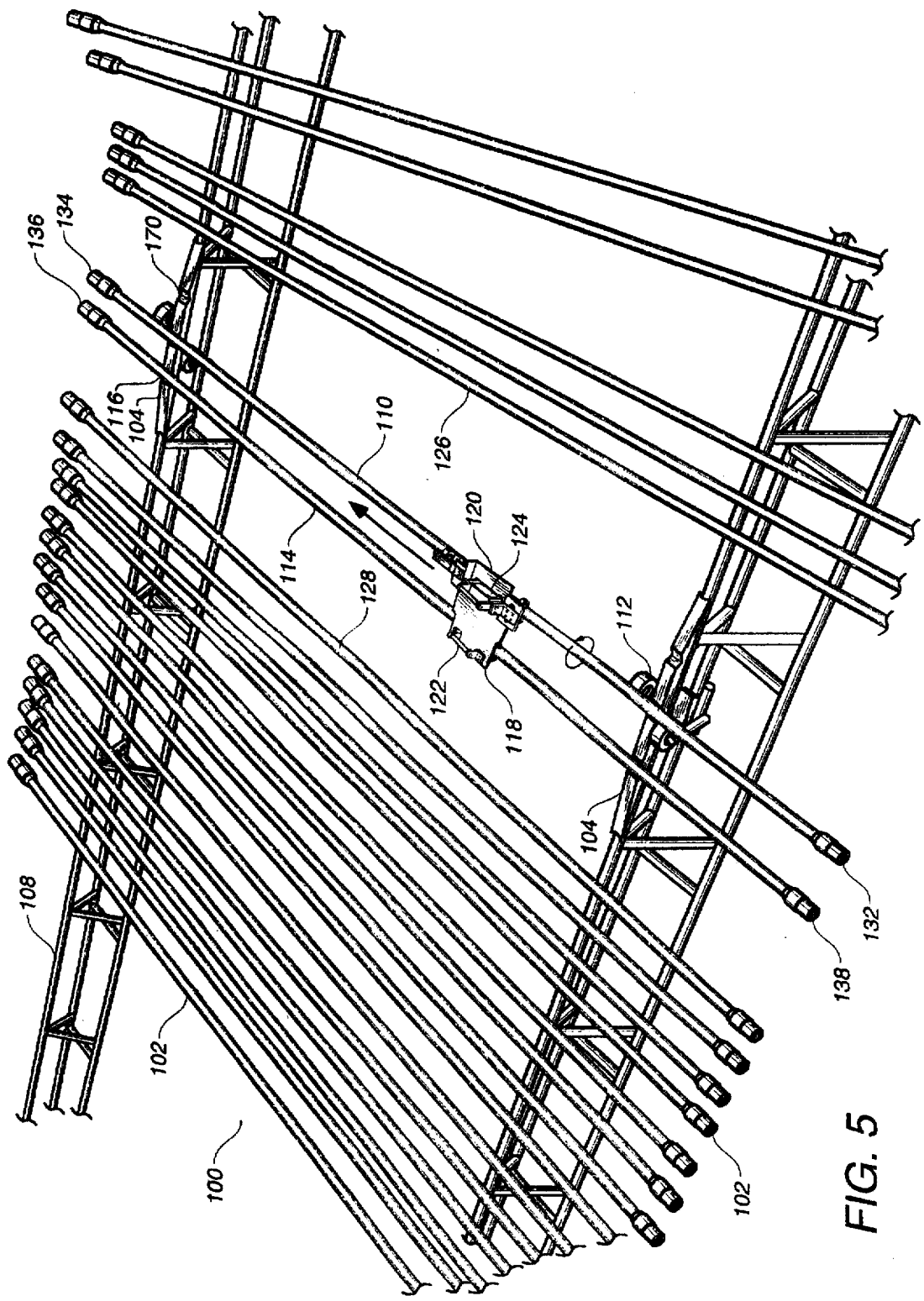
FIG. 5 is a perspective view of the method of the system of the present invention showing, in particular, the method of inspecting tubular member.

FIG. 5 is illustrative of the method 100 of the present invention for the non-destructive inspection of tubular members. Initially, in FIG. 5, it can be seen that the tubular members 102 are supported on the top surface of a tubular member support rack 104. The tubular member support rack 104 is mounted onto the top surface of a first rail 106 and a second rail 108. The rails 106 and 108 are positioned in parallel alignment. Each of the tubular members 102 are supported on the rails 106 and 108.

Initially, in FIG. 5, it can be seen that a tubular member 110 is received within a drive roller 112 on the tubular member support rack 104. The drive roller 112 serves to impart rotational movement to the tubular member 110. A second tubular member 114 is positioned in generally parallel relationship to the tubular member 110 on the tubular member support rack 104. A notch 116 can be formed in the support rack 104 so that the second tubular member 114 can be placed a desired distance from the first tubular member 110.

Importantly, it can be seen that the cart 118 is placed onto the top surface of the tubular members 110 and 114. The pairs of wheels on one side 120 of the cart 118 contact the surface of the first tubular member 110. The bearings on the other side 122 of the cart 118 are positioned onto a surface of the second tubular member 114. The inspection unit 124 is positioned on the top surface of the cart 118 so as to allow for the ultrasonic inspection of first tubular member 110.

In the method of the present invention, the first tubular member 110 is initially rolled along the rails 106 and 108 until the tubular member 110 is positioned into the drive roller 112 on the support rack 104. Next, the second tubular member 114 is rolled along the rails 106 and 108 until it is placed into the notch 116 on the support rack 104 so as to be in a proper position in parallel relationship to the first tubular member 110.

The inspection cart 108 is then placed onto the first tubular member 110 and onto the second tubular member 114 such that the wheels of the inspection cart 118 contact a surface of the first tubular member 110 and the bearings of the cart 118 contact the surface of the second tubular member 114. The first tubular member 110 is rotated by the drive roller 112 such that the inspection cart 118 moves longitudinally along the first tubular member 110 and the second tubular member 114. While the cart 118 traverses the length of the tubular members 110 and 114, the ultrasonic inspection unit 124 transmits and receives inspection data relative to the structure of the tubular member 110.

After the inspection cart 118 has transversed the desired length of the tubular members 110 and 114, the handles of the inspection cart 118 are grabbed so that the inspection cart 118 can be lifted from the tubular members 110 and 114. After the inspection cart 118 is removed, the first tubular member 110 is removed from the drive roller 120 and will move to an opposite side of the drive roller (as shown by tubular member 136 in FIG. 5). The second tubular member 114 is then moved from its position in notch 116 into the drive roller 112. A third tubular member 128 is then rolled into generally parallel relationship to the second tubular member 114 and is positioned in the notch 116. The inspection cart 118 can then be placed onto the second tubular member 114 and the third tubular member 128 such that the wheels of the inspection cart 118 contact a surface of the second tubular member 114 and the bearings of the inspection cart 118 contact the surface of the third tubular member 128. The second tubular member 114 is then rotated such that the inspection cart moves longitudinally along the second tubular member 114 and the third tubular member 128. Ultrasonic inspection data is transmitted from and received by the inspection unit 124 as the inspection cart 118 moves along the second tubular member 114. After this procedure is completed and the cart 118 traverses the length of the second tubular member 114, the second tubular member 114 can be removed from the drive roller 112 and moved to the other side of the drive roller. The process can continue for all of the tubular members 102 on the tubular member support rack 104.

In the present invention, it is possible to avoid the necessity of bringing the inspection cart 118 back to the same starting point on each of the tubular members which are tested. In particular, it is possible to place the inspection cart 118 at the opposite end of the tubular member from that where the inspections started on the previous tubular member. This can be accomplished by changing the direction of rotation of the drive roller 112 such that the second tubular member 114 rotates in an opposite direction than did the first tubular member 110. In other words, the inspection unit 118 initially moves from end 132 of the first tubular member 110 to the opposite end 134 of the first tubular member 110. When the inspection cart 118 is placed onto the second tubular member 114 and the third tubular member 128, the inspection cart 118 will move from the end 136 of the second tubular member 114 to the end 138 of the second tubular member 114. As such, the present invention enhances the efficiency of the inspection process. Furthermore, within the concept of the present invention, another notch can be formed in the support rack 104 so that tubular members on the opposite side of the drive roller 112 can be positioned properly for inspection.

Figure 6:
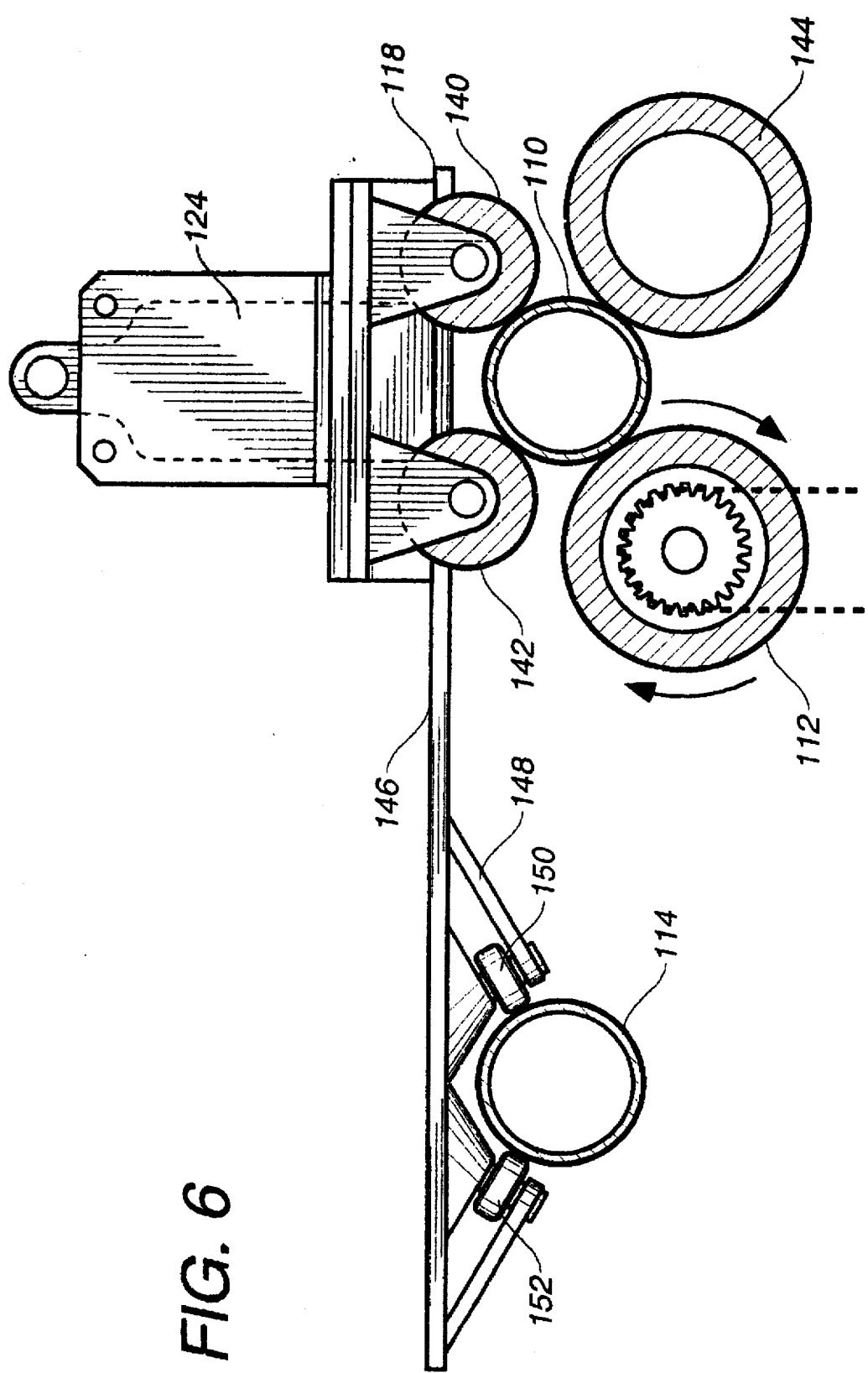
FIG. 6 is a cross-sectional side view of the inspection cart as placed on the rotatable tubular member in accordance with the method of the present invention.

FIG. 6 shows a detailed view of the operation of the drive roller 112 relative to the movement of the inspection cart 118. Initially, in FIG. 6, it can be seen that the wheels 140 and 142 contact the surface of the tubular member 110. The drive roller 112 is a chain driven drive roller such that a motor is provided which will rotate the drive roller 112 in a desired direction. As the roller 112 rotates, it will rotate the tubular member 110 in an opposite direction. The tubular member 110 is supported on its opposite side by a free roller 144. The counterclockwise rotation of the tubular member 110 will cause each of the wheels 140 and 142 to rotate in a clockwise direction. Since the wheels 140 and 142 are canted such that their axes of rotation are canted at an angle relative to the longitudinal axis of the tubular member 110, the cart 118 and associated inspection unit 124 will move longitudinally along the length of the tubular member 110.

In FIG. 6, it can be seen that the cart 118 has platform 146 formed thereon. At the opposite end of the platform 146 from the wheels 140 and 142 is a bearing arrangement 148. The bearing arrangement 148 includes a first roller 150 and a second roller 152 for supporting the platform 146 a desired distance above the tubular member 114. The first roller 150 has an axis of rotation which is transverse to the longitudinal axis of the tubular member 114. Similarly, the second roller 154 has an axis or rotation which is transverse to the longitudinal axis of the tubular member 114. Each of the rollers 150 and 152 are free rollers which allow the platform 146 to move linearly along the length of the tubular member 114. Each of the rollers 150 and 152 will rotate during the movement of the platform 146 along the tubular members 110 and 114. Since the rollers 150 and 152 are not driven, the rollers 150 and 152 serve to support the platform 146 and to allow the platform 146 to roll along the length of the second tubular member 114.

Figure 7:
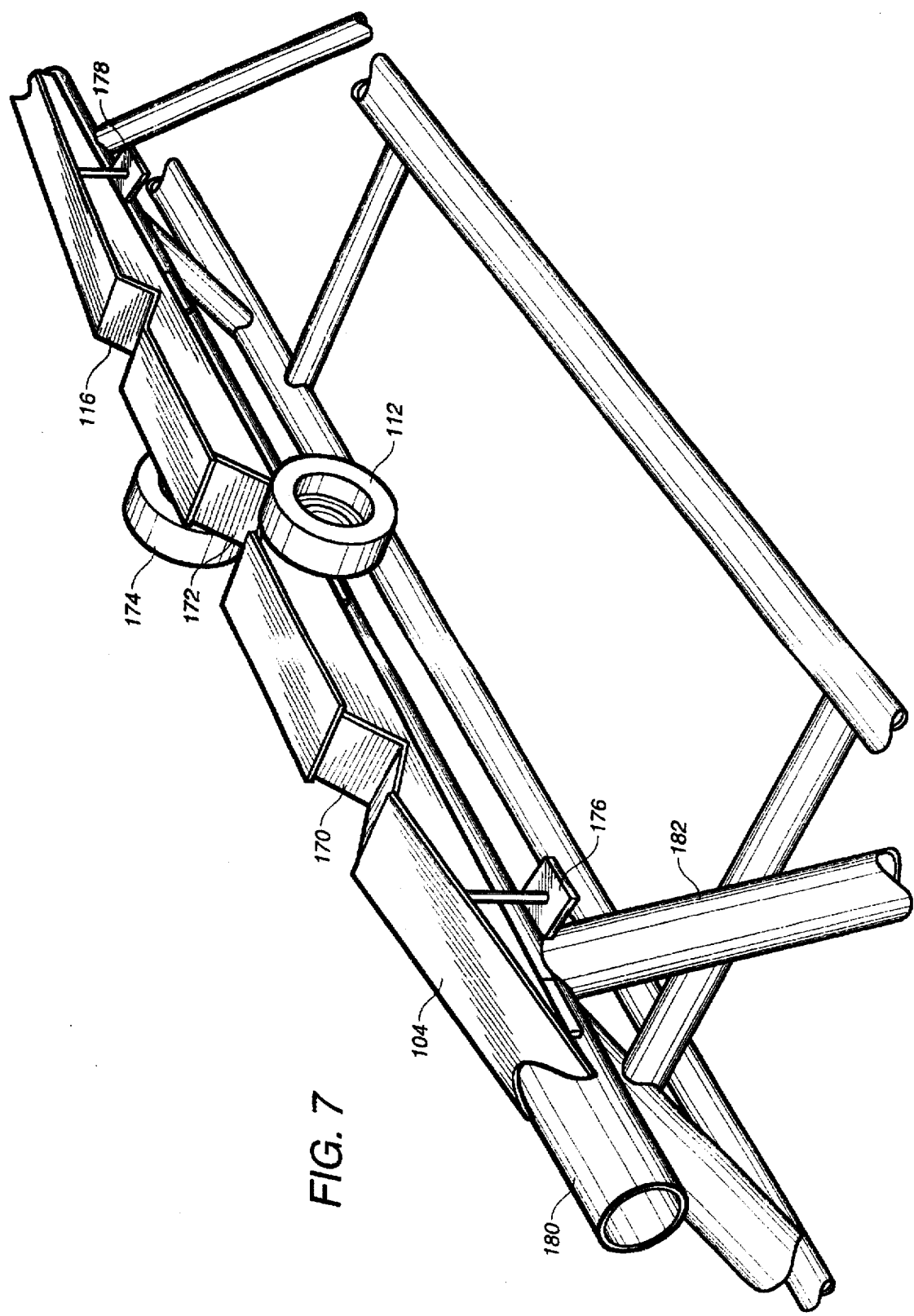
FIG. 7 is a perspective view showing the drive rollers and tubular member support rack as attached to a tubular member stand.

Referring to FIG. 7, the structure of the tubular member support rack 104 is illustrated with particularity. As can be seen, the tubular member support rack 104 includes notch 116 and notch 170 on opposite sides of the drive roller 102. Each of the notches 116 and 170 serves to allow a tubular member to be positioned in generally parallel and properly spaced relationship from the tubular member residing in notch 172. The tubular member which is received within notch 172 is the "driven" tubular member. Rotation to the tubular member is imparted by way of the drive roller 112 and the drive roller 174. Any rotational movement imparted by either of the drive rollers 112 and 174 to the tubular member received within the notch 172 will cause the tubular member to rotate, as described herein previously.

Importantly, it can be seen that the tubular member support rack 104 is mounted by clamps 176 and 178 onto the top surface 180 of the tubular member stand 182. As such, the configuration of the present invention can be applied onto conventional tubular member stands. It is simply necessary to loosen the clamps 176 and 178 such that the tubular member support rack 104 can be installed onto a top surface of a tubular member stand 182. A corresponding support rack can be applied to the opposite rail of the tubular member stand. The opposite tubular member support rack will have a similar configuration as that shown in FIG. 7, but for the drive rollers 112 and 174.

In the present invention, the tubular member which is actually being inspected serves as a "bridge" for moving the inspection unit along the entire length of the tubular member. The present invention allows the same material which is inspected to act as a bridge on which the inspection cart runs the entire length of the tubular member. As such, it is not necessary to have expensive equipment available which must be used for the inspection of tubular members. Furthermore, the present invention allows the hand-held inspection units (which are currently used for the inspection of the ends of the pipe) to be used effectively for the entire length of the tubular member.

The foregoing disclosure and description of the invention is illustrative and explanatory thereof. Various changes in the details of the illustrated configuration or in the steps of the described method may be made within the scope of the appended claims without departing from the true spirit of the invention. The present invention should only be limited by the following claims and their legal equivalents.

I claim:

1. A system for ultrasonic inspection comprising:
   a first tubular member;
   a second tubular member in parallel relation to said first tubular member;
   a means for rotating said first tubular member;
   an ultrasonic inspection unit;
   a platform having a means formed thereon for receiving said ultrasonic inspection unit;
   a first wheel means connected to said platform, said first wheel means contacting a surface of said first tubular member, said first wheel means for moving said platform along and around said first tubular member relative to a rotation of said first tubular member; and
   a bearing means connected to said platform at a location distal said first wheel means, said bearing means contacting said second tubular member, said bearing means for supporting said platform on said second tubular member and for allowing said platform to move longitudinally along said second tubular member in correspondence with the moving of said first wheel means.

2. The system of claim 1, said first wheel means comprising:
   first pair of wheels positioned at one end of said platform, said first pair of wheels having an axis of rotation which is canted at an angle relative to a longitudinal axis of said first tubular member.

3. The system of claim 2, said first wheel means comprising:
   a second pair of wheels positioned at an end of said platform opposite said first pair of wheels, said second pair of wheels being canted at the same angle as said first pair of wheels relative to the longitudinal axis of said first tubular member.

4. The system of claim 2, said first pair of wheels being rotatably supported below a bar, said bar being adjustably pivotally connected to said platform so as to change the angle of cant to a desired angle.

5. The system of claim 4, said platform having a first arcuate slot and a second arcuate slot formed therein, said bar having a first guide member extending upwardly through said first arcuate slot and a second guide member extending upwardly through said second arcuate slot, said first guide member having a means for fixing a position of said first guide member in said first arcuate slot, said second guide member having a means for fixing a position of said second guide member in said second arcuate slot.

6. The system of claim 1, further comprising:
   sensor wheel means extending outwardly from said platform, said sensor wheel means being rotatable during the moving of said platform along said first tubular member, said sensor wheel means for transmitting ultrasonic signals into said first tubular member.

7. The system of claim 6, said sensor wheel means comprising:
   a sensor wheel rotatably mounted onto an arm extending outwardly of said platform, said sensor wheel having a surface extending downwardly from said arm so as to contact said first tubular member.

8. The system of claim 7, said first wheel means having an axis of rotation which is canted at an angle relative to a longitudinal axis of said first tubular member, said sensor wheel means having an axis of rotation which is canted at the same angle as said first wheel means.

9. The system of claim 1, said platform having at least one handle member affixed to said platform and extending upwardly from said platform.

10. The system of claim 3, said means for receiving an ultrasonic inspection unit being formed between said first pair of wheels and said second pair of wheels generally adjacent to a surface of said first tubular member.

11. The system of claim 1, said first wheel means being connected to one side of said cart, said bearing means being connected to an opposite side of said cart, said bearing means comprising:
    a first roller rotatably connected to said platform and extending downwardly from said platform, said first roller having a surface contacting a surface of the second tubular member, said first roller having an axis of rotation transverse to a longitudinal axis of the second tubular member.

12. The system of claim 11, said bearing means further comprising:
    a second roller rotatably connected to said platform and extending downwardly from said platform, said second roller having a surface contacting said second tubular member, said second roller being radially offset from said first roller relative to said second tubular member, said second roller having an axis of rotation transverse to the longitudinal axis of said second tubular member.

13. An inspection system comprising:
    a rack;
    a first tubular member;
    a tubular member rotation means connected to said rack, said tubular member rotation means receiving said first tubular member, said tubular member rotation means for rotating said first tubular member about a longitudinal axis of said first tubular member;
    a second tubular member supported on said rack a desired distance from said first tubular member, said second tubular member being in generally parallel relationship to said first tubular member;
    a platform being supported on said first tubular member by a first wheel means, said first wheel means contacting a surface of said first tubular member, said first wheel means connected to said platform so as to move said platform along and around said first tubular member as said tubular member rotation means rotates said first tubular member, said second tubular member supporting a surface of said platform; and
    a non-destructive inspection means mounted on said platform for ultrasonically inspecting said first tubular member.

14. The system of claim 13, further comprising:
    a bearing means connected to said platform distal of said first wheel means, said bearing means for supporting said platform above said second tubular member and for allowing said platform to move longitudinally along said second tubular member in correspondence with the moving of said first wheel means on said first tubular member.

15. The system of claim 13, said first wheel means comprising:
- a first pair of wheels positioned at one end of said platform, said first pair of wheels having an axis of rotation which is canted at an angle relative to a longitudinal axis of said first tubular member; and
- a second pair of wheels positioned at an end of said platform opposite said first pair of wheels, said second pair of wheels being canted at the same angle as said first pair of wheels relative to the longitudinal axis of said first tubular member.

16. The system of claim 13, further comprising:
- a sensor wheel means extending outwardly from said platform, said sensor wheel means being rotatable during the moving of said platform along said first tubular member, said sensor wheel means for transmitting ultrasonic signals.

17. The system of claim 16, said sensor wheel means comprising:
- a sensor wheel rotatably mounted onto an arm extending outwardly of said platform, said sensor wheel having a surface extending downwardly from said arm so as to contact said first tubular member, said first wheel means having an axis of rotation which is canted at an angle relative to said longitudinal axis of said first tubular member, said sensor wheel having an axis of rotation which is canted at the same angle as said first wheel means.

18. A method of ultrasonic inspection comprising the steps of:
- placing a first tubular member onto a drive roller of a tubular member support rack;
- positioning a second tubular member in generally parallel relationship to said first tubular member on said tubular member support rack;
- placing an inspection cart onto said first tubular member and onto said second tubular member such that said inspection cart has a pair of canted wheels contacting a surface of said first tubular member and a bearing contacting a surface of said second tubular member, said inspection cart having a non-destructive inspection unit mounted thereon;
- rotating said first tubular member such that said inspection cart moves around and along said first tubular member and along said second tubular member; and
- transmitting ultrasonic inspection data from said inspection unit as said inspection cart moves along said first tubular member.

19. The method of claim 18, further comprising the steps of:
- lifting said inspection cart from said first and second tubular members after said inspection cart reaches a desired destination on said first tubular member;
- removing said first tubular member from said drive roller;
- moving said second tubular member onto said drive roller;
- positioning a third tubular member into generally parallel relationship with said second tubular member on said tubular member support rack;
- placing said inspection cart onto said second tubular member and onto said third tubular member such that said pair of canted wheels contact said second tubular member and said bearing contacts a surface of said third tubular member;
- rotating said second tubular member such that said inspection cart moves longitudinally along said second tubular member and said third tubular member; and
- transmitting ultrasonic inspection data from said inspection unit as said inspection cart moves along said second tubular member.

\* \* \* \* \*